| United States Patent [19] | [11] Patent Number: 5,051,502 |
| Miller et al. | [45] Date of Patent: Sep. 24, 1991 |

[54] RHODIUM CATALYZED CYCLIZATION PROCESS FOR BICYCLIC β-LACTAMS

[75] Inventors: Marvin J. Miller, South Bend; Matthew A. Williams, Mishawaka, both of Ind.

[73] Assignee: University of Notre Dame du Lac, Notre Dame, Ind.

[21] Appl. No.: 534,073

[22] Filed: Jun. 6, 1990

[51] Int. Cl.$^5$ ............... C07D 205/085; C07D 205/08; C07D 487/04

[52] U.S. Cl. .................................. 540/205; 540/302; 540/355

[58] Field of Search ............................... 540/205, 302

[56] References Cited

PUBLICATIONS

Padwa, J. Org. Chem. 55, 405 (1990).

Primary Examiner—Mark L. Berch
Attorney, Agent, or Firm—William B. Scanlon; Leroy Whitaker

[57] ABSTRACT

1-Carbapenam-2-one-3-carboxylic acid and 1-carba-3-hydroxy-3-cephem-4-carboxylic acid and esters thereof are provided by a process comprising a rhodium $C_2$–$C_{10}$ carboxylate catalyzed cyclization of an ester of a 4-(1-alkoxy- or 1-substituted alkxoy)-2-oxo-4-azetidinyl)-α-diazo-β-ketobutyric acid and an ester of a 5-(1-alkoxy- or 1-substituted alkoxy-2-oxo-4-azetidinyl)-α-diazo-β-ketovaleric acid respectively. The process is carried out in an inert organic solvent at a temperature between about 15° C. and about 85°0 C. The 1-carba bicyclic β-lactams are intermediates for preparing antibiotics.

14 Claims, No Drawings

RHODIUM CATALYZED CYCLIZATION PROCESS FOR BICYCLIC β-LACTAMS

BACKGROUND OF THE INVENTION

This invention relates to bicyclic β-lactam compounds. In particular it relates to a process for preparing fused bicyclic β-lactam 1-carbapenams and 1-carbacephems and to intermediates useful therein.

Many synthetic approaches for the preparation of bicyclic β-lactams have been described. Generally these methods involve the formation of a bicyclic ring system from an appropriately substituted azetidinone ring. One such method involves the treatment of an α-diazo-β-ketoester substituted azetidinone with rhodium acetate catalyst. For example, an azetidinone substituted in the 4-position by a α-diazo-β-oxo butan-4-yloic acid methyl ester group [—$CH_2$—C(O)—CH($N_2$)—$COOCH_3$] and wherein the azetidinone ring nitrogen is unsubstituted results in carbapenam ring formation by the so-called rhodium acetate catalyzed "diazo insertion." This method has been applied to the preparation of the carbapenam ring system such as that of the antibiotic thienamycin, Ratcliffe, R. W.; Salzmann, T. N.; Christensen, B. G., Tetrahedron Lett. 1980, 21, 31, and to the preparation of 1-carbacephems, Evans, D. A.; Sjogren, E. B., Tetrahedron Lett. 1985, 26, 3789. Prior to this invention all such diazo insertion reactions were carried out on the unsubstituted ring nitrogen atom (N—H) resulting in cyclization in varying yields. We have discovered that azetidinones substituted on the ring nitrogen by an alkoxy group or a substituted alkoxy group represented by the general formula

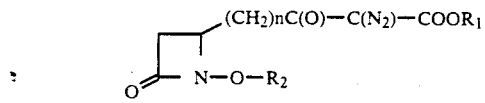

wherein n is 1 or 2, undergo facile cyclization with catalytic amounts of rhodium $C_2$–$C_{10}$ carboxylates e.g. rhodium tetraacetate.

The process of this invention thus provides a route to the bicyclic 1-carbapenams and 1-carbacephems from N-substituted azetidinones obtained from the hydroxamate mediated formation of β-lactams, Miller, M. J., Accts. Chem. Res. 1986, 19, 49; Rajendra, G., Miller, M. J., Tetrahedron Lett., 1987, 28, 6257.

SUMMARY OF THE INVENTION 1-carbapenams and 1-carbacephems represented by the formula 1

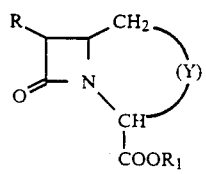

wherein R is hydrogen, amino, protected amino, ethyl or hydroxyethyl; $R_1$ is a carboxy protecting group and Y is a divalent radical represented by the formula

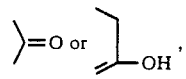

are provided in a process which comprises treating an N-alkoxy or N-substituted alkoxy azetidinone represented by the formula A

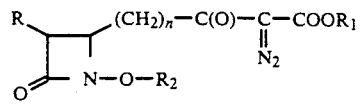

in an inert solvent with a catalytic amount of a rhodium $C_2$–$C_{10}$ carboxylate where, in the formula A, R and $R_1$ have the same meanings as defined above, n is 1 or 2; and $R_2$ is an alkyl group such as methyl or a substituted alkyl group such as benzyl.

DETAILED DESCRIPTION

According to the process of this invention the α-diazo-β-ketoester represented by the formula A is converted to the bicyclic β-lactam represented by the formula 1 by catalysis with a rhodium $C_2$–$C_{10}$ carboxylate. The bicyclic β-lactam provided in the process, when Y of the formula 1 is >=O, is a 1-carbapenam represented by the formula

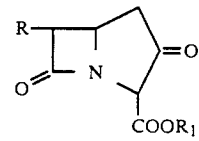

or when Y of the formula 1 is

a 1-carba-3-hydroxy-3-cephem represented by the formula

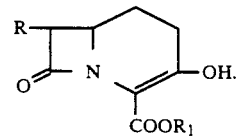

The process is carried out in an inert solvent at a temperature between about 15° C. and about 85° C. and preferably at about 45° C. to about 65° C. in the presence of a catalytic amount of the rhodium catalyst. Inert solvents which may be used are organic solvents or mixed organic solvents which are unreactive towards the α-diazo-β-ketoester, the product and the rhodium catalyst. Typical solvents are the halogenated hydrocarbons such as methylene chloride, trichloroethane, dichloroethane, chloroform and the like; aromatic hydrocarbons such as benzene, toluene and xylenes; ethers such as tetrahydrofuran, diethyl ether, or dioxane, and the like.

The process is carried out in the presence of a catalytic amount of the rhodium carboxylate. A catalytic amount includes preferably amounts of between about 1 mole percent to about 10 mole percent relative to the amount of α-diazo-β-ketoester employed in the process. Generally the process proceeds best with about 5 mole percent of the catalyst. Amounts of catalyst lower than 1 mole percent can be used however, the reaction proceeds best with amounts above about 3 mole percent. If the original amount of the catalyst is insufficient an additional amount may be added during the process.

Rhodium $C_2$-$C_{10}$ carboxylates which are used in the process are for example rhodium tetraacetate $Rh_2(OAc)_4$, rhodium tetrapropionate, rhodium octanoate and rhodium decanoate. Preferred rhodium catalysts are rhodium acetate and rhodium octanoate. Rhodium tetraacetate is an especially preferred catalyst of the invention.

The process is carried out by dissolving the α-diazo-β-ketoester in the solvent, adding the catalyst and then heating the mixture. The mixture is stirred well or otherwise agitated e.g. by shaking or sonication. For example, the α-diazo-β-ketoester, t-butyl 4-(1-benzyloxy-2-oxo-3-protected amino-4-azetidinyl)-α-diazo-β-ketobutyrate is dissolved in methylene chloride and the solution is treated with about 5 mole percent of rhodium tetraacetate. The mixture is stirred and heated to the reflux temperature for about 5 to about 6 hours. The catalyst is filtered and the filtrate is evaporated to dryness. The product can be recovered from the residue and purified by chromatography on a suitable material such as silica. During the course of the process the process mixture may be monitored by thin layer chromatography on silica plates of small aliquots withdrawn from time to time.

The α-diazo-β-ketoester substituted azetidinone used as the starting material in the process is represented by the formula A wherein R is hydrogen, ethyl or hydroxyethyl, preferably 1-hydroxyethyl, amino or a protected amino group; $R_1$ is a carboxy protecting group; $R_2$ is an alkyl group or a substituted alkyl group; and n is 1 or 2.

The term "protected amino group" refers to an amino group substituted by a conventional amino protecting group or by an acyl or diacyl group. For example R can be an amino group substituted by an alkoxy, cycloalkoxy, alkenyloxy, alkynyoxy or aralkoxy group represented by the formula $R_3OC(O)-$ wherein $R_3$ is $C_1$-$C_6$ alkyl, $C_3$-$C_5$ alkenyl, $C_3$-$C_5$ alkynyl, $C_3$-$C_6$ cycloalkyl, arylmethyl or diarylmethyl. Examples of such groups are methoxycarbonyl, ethoxycarbonyl, t-butyloxycarbonyl, amyloxycarbonyl, allyloxycarbonyl, 2-butenyloxycarbonyl, propargyloxycarbonyl, 1,1-dimethylpropynyloxycarbonyl, cyclopropyloxycarbonyl, cyclopentyloxycarbonyl, cyclohexyloxycarbonyl, benzyloxycarbonyl, 4-nitrobenzyloxycarbonyl, and diphenylmethoxycarbonyl.

The protected amino group may be a diacylamino group such a phthalimido or succinamido; or an acylamino group wherein the acyl group can be $C_1$-$C_6$ alkanoyl, such as acetyl or propionyl; an arylacetyl or heterocyclicacetyl group such as phenylacetyl, phenoxyacetyl, 2-thienylacetyl or 2-furylacetyl and the like. The trityl group (triphenylmethyl) and the 4,5-diphenyl-4-oxazolin-2-one-yl group ("Ox protecting group") are likewise suitable amino protecting groups.

The term "carboxy protecting group" refers to ester moieties commonly used in organic chemistry for the temporary protection of the carboxylic acid function. Examples of such groups represented by $R_1$ are $C_1$-$C_4$ alkyl, such as methyl, ethyl and t-butyl; arylmethyl and diarylmethyl e.g. benzyl, 4-methoxybenzyl, 4-nitrobenzyl, diphenylmethyl, 4-methoxydiphenylmethyl and 4,4'-dimethoxydiphenylmethyl; haloalkyl groups such as trichloromethyl, and dichloromethyl; phenacyl; allyl; trialkylsilyl groups such as trimethylsilyl and t-butyldimethylsilyl, the 2-(trimethylsilyl)ethyl; and like conventional carboxy protecting groups.

The term $R_2$ of the formula A is an alkyl or substituted alkyl group. Preferably $R_2$ is a $C_1$-$C_6$ alkyl group or a substituted $C_1$-$C_6$ alkyl group wherein the carbon bonded to the oxygen atom also bears a hydrogen atom. Otherwise, the alkyl chain may be branched and/or substituted. Examples of such alkoxy groups $R_2O-$ of the formula 1 are methoxy, ethoxy, isopropoxy, n-butoxy, sec-butoxy, n-amyloxy, and the like. "Substituted alkyl" refers to a $C_1$-$C_6$ alkyl group substituted by phenyl, carboxy which may be a protected carboxy group as defined above, hydroxy, fluoro, chloro or bromo, cyano, or $C_1$-$C_3$ alkoxy. Examples of $R_2O$ groups wherein $R_2$ is substituted $C_1$-$C_6$ alkyl are benzyloxy, 2-phenylethoxy, 4-methoxybenzyloxy, 2-hydroxyethoxy, 3-hydroxypropoxy, 5-hydroxyhexyloxy, methoxymethyl, 2-methoxyethoxy, ethoxymethoxy, 4-methoxybutoxy, 2-chloroethoxy, 3-bromoethoxy, fluoromethoxy, carboxymethoxy, ethoxycarbonylmethoxy, t-butyloxycarbonylmethoxy, 1-carboxyethoxy, 3-carboxypropoxy, cyanomethoxy, 2-cyanoethoxy, and like substituted groups. Preferred $R_2$ groups are benzyl, methyl and carboxymethyl especially protected carboxymethyl such as t-butyloxycarbonylmethyl, methoxycarbonylmethyl or benzyloxycarbonylmethyl.

The predominant side product of the process is the aldehyde formed from the $R_2O$ group on the azetidinone ring nitrogen. For example when $R_2O$ is benzyloxy, benzaldehyde is formed in the process. Although we do not wish to be bound by any particular theory the following mechanism appears to be consistent with the observed products of the process wherein a penam is formed.

Initially, the carbenoid generated by the loss of nitrogen from the diazo group may interact electrophilically with the N-alkoxylactam lone electron pair to give the ylide intermediate shown below. Next, abstraction of a proton from the carbon atom alpha to the oxygen atom of $R_2O$ of the ylide is followed by N—O bond heterolysis.

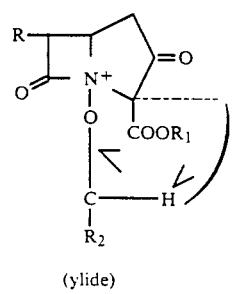

(ylide)

Prior to this invention the known "diazo-insertion" reaction required an unsubstituted ring nitrogen of the β-lactam ring.

In one of its aspects, this invention provides the intermediates (formula A) useful in the process of the invention. Examples of α-diazo-β-ketoesters (formula A) which are used in the process to provide the 1-carbapenams and 1-carbacephams (formula 1) are shown in the following Table 1 wherein the terms R, $R_1$, $R_2$, and n refer to formula A above.

TABLE 1

| α-Diazo-β-Ketoesters | | | |
|---|---|---|---|
| R | $R_1$ | $R_2$ | n |
| amino | methyl | benzyl | 1 |
| amino | methyl | benzyl | 2 |
| 1-hydroxyethyl | t-butyl | methyl | 1 |
| ethyl | t-butyl | benzyl | 1 |
| phenylacetylamino | benzyl | ethyl | 2 |
| phenylacetylamino | benzyl | benzyl | 1 |
| phenylacetylamino | benzyl | carboxymethyl | 2 |
| phenylacetylamino | benzyl | ethoxycarbonyl-methyl | 2 |
| benzyloxycarbonyl-amino | methyl | cyanomethyl | 1 |
| benzyloxycarbonyl-amino | diphenylmethyl | t-butyloxycarbonyl-methyl | 2 |
| tritylamino | 4-methoxybenzyl | benzyl | 1 |
| tritylamino | 4-methoxybenzyl | benzyl | 1 |
| tritylamino | 4-methoxybenzyl | n-propyl | 1 |
| t-butyloxycarbonyl-amino | trimethylsilyl | 4-nitrobenzyl | 1 |
| phenoxyacetylamino | 4-methoxybenzyl | benzyl | 2 |

The α-diazo-β-ketoesters are prepared by known methods. For example, compound A wherein R is an amino group or a protected amino group and n=1 is obtained from an α-amino-or(α-protected amino)-β-hydroxy glutaric acid mono ester. The mono ester is converted to an O-alkyl or O-substituted alkyl amide by reaction with an O-alkyl or O-substituted hydroxylamine, e.g. methoxyamine or benzyloxyamine, and the derivative is cyclized under the conditions described by Miller, M. J., et al., J. Am. Chem. Soc. 1980, 102, 7026 to provide the β-lactam, a 1-alkoxy or substituted alkoxy-3-amino (or substituted amino)-4-carboxymethylazetidine-2-one. The 4-carboxymethyl group of the azetidinone is homologated to the β-keto ester via the Masamune procedure, Brooks, D. W., et al., Angew. Chem., Int. Ed. Engl. 1979, 18, 72. The β-ketoester is then converted to the α-diazo derivative with tosyl azide or p-carboxyphenylsulfonyl azide.

The compound A wherein n=2 is obtained in like manner with an α-amino-β-hydroxyadipic acid mono ester.

A preferred group of α-diazo-β-keto esters A are represented when $R_2$ is $C_1$ alkyl, especially methyl, or a substituted $C_1$–$C_6$ alkyl group substituted by phenyl, especially benzyl and substituted benzyl eg. 4-methoxybenzyl. Another preferred group is represented when $R_2$ is an esterified carboxymethyl group such a t-butyloxycarbonylmethyl, methoxycarboxylmethyl and benzyloxycarbonylmethyl. Further preferred compounds are represented when $R_2$ is $C_1$–$C_6$ alkyl substituted by $C_1$–$C_3$ alkoxy, for example compounds wherein $R_2$ is methoxymethyl, ethoxymethyl, 2-methoxyethyl, 1-methoxyethyl, and the like. Also preferred are compounds represented by the formula A wherein R is amino, protected amino, and n is 2 or R is ethyl or 1-hydroxyethyl and n is 1.

The 1-carbapenam-2-one-3-carboxylic acids and esters provided by the process are useful intermediates for the preparation of antibiotic compounds such as thienamycin and PS-5. The 1-carba-3-hydroxy-3-cephem-4-carboxylic acids and esters are useful intermediates in the preparation of 1-carba-3-chloro-3-cephem-4-carboxylic acid antibiotics such as loracarbef, 7β-(phenylglycylamino)-3-chloro-1-carba-3-cephem-4-carboxylic acid, U.S. Pat. No. 4,708,956.

The following Preparations and Examples further describe the invention but are not intended to be limiting thereof.

$^1$H NMR and $^{13}$C NMR spectra were obtained at 300 MHz and 75 MHz respectively on a General Electric GN-300 spectrometer in chloroform-d. $^1$H NMR spectra are referenced to internal tetramethylsilane. $^{13}$C NMR spectra are referenced to the center peak of the chloroform-d triplet at 77.00 ppm. Mass spectra (MS) were recorded on a Finnagan MAT Model 8430 spectrometer using electron impact ionization (70 eV) or if indicated, chemical ionization (CIMS) with ammonia. IR spectra were taken on a Perkin-Elmer Model 1420 spectrometer and referenced to polystyrene at 1601 cm$^{-1}$. Flash chromatographic separations were performed with silica gel 60, 230–400 mesh (EM Science). TLC analysis was performed on aluminum-backed silica gel 60 $F_{254}$, 0.2 mm plates (MCB Reagents) and visualized with UV light or ethanolic phosphomolybdic acid followed by heating. Anhydrous $CH_2Cl_2$, pyridine, and acetonitrile were prepared by distillation from calcium hydride. $CrO_3$ was vacuum desiccated over $P_2O_5$ for 24 h before use.

Preparation 1

Methyl 4-(1-benzyloxy-2-oxo-4-azetidinyl)-α-diazo-β-ketobutyrate

A. Preparation of β-ketoester, β-(t-butyldimethylsilyloxy)-δ-oxopimelic acid methyl benzyl diester Crystalline mono methyl ester of β-(t-butyldimethylsilyloxy) glutaric acid, prepared according to Rosen, T. et al., J. Org. Chem. 1984, 49, 3657, (8.55 g, 31 mmol) in THF was treated with carbonyldimidazole (5.53 g, 34 mmol) and allowed to stir 3 hr. at room temperature. In a separate flask, monobenzylmalonate (7.18 g, 37 mmol) was dissolved in THF (60 ml) and cooled to −78° C., and dibutylmagnesium (37 ml of a 0.5M solution in heptane, 18.5 mmol) was added via syringe over a 5 min period. A white precipitate formed. This mixture was stirred for 15 min at −78° C. and then for 1.5 hr. at room temperature. The solvent was removed in vacuo and the solution of the acyl imidazole was added via cannula to the residue of the magnesium salt. This nonhomogeneous mixture was stirred for 42 hr. at room temperature and then for 24 hr. at 35° C. The THF was removed in vacuo and the residue taken up in $Et_2O$ (300 ml) and washed with 10% citric acid (2×100 ml), saturated $NaHCO_3$ (2×100 ml) and dried ($MgSO_4$). Removal of solvent in vacuo gave 12.4 g of crude product which was flash chromatographed on silica (5:1 hexanes/ethyl acetate) to yield 10.87 g (86%) of the β-ketoester as a colorless oil. $R_f$=0.38(3:1 hexanes/ethyl acetate) IR (thin film) 2960, 2940, 2860, 1745, 1720 cm$^{-1}$.

$^1$H NMR (CDCl$_3$) 0.03(s, 3H), 0.06 (s,3H), 0.83 (s,9H), 3.51 (s, 2H), 3.65 (s, 3H), 4.57 (m, 1H), 5.17 (s, 2H), 7.35 (m, 5H).

$^{13}$C (CDCl$_3$) −5.25, 17.61, 25.46, 41.84, 49.73, 50.07, 51.19, 65.25, 66.77, 128.11, 128.15, 128,32, 135.15, 166.39, 170.90, 200.37.

B. Preparation of β-(t-butyldimethylsilyloxy)-δ-hydroxypimelic acid methyl benzyl diester To the β-ketoester 9.34 g, 22.9 mmol) in methanol (50 ml) at 0° C. was added NaBH$_4$ (886 mg, 22.9 mmol) portionwise over a 5 min period. After 15 min the reaction was diluted with brine (100 ml) and extracted with ethyl acetate (2×100 ml). The organic layers were combined, dried (MgSO$_4$), the solvent removed in vacuo, and the residue purified by flash chromatography (6:1 hexane/acetone). After rechromatography of mixed fractions to remove a faster moving impurity identified as benzyl alcohol, 7.27 g (84%) of the alcohol were obtained as a 2:1 mixture of diastereomers. R$_f$=0.29(3:1 hexanes/acetone) were obtained.

IR (thin film) 3520 (broad) 2960, 2940, 2900, 2860, 1740, 1255, 1165, 1080 cm$^{-1}$.

$^1$H NMR (CDCl$_3$) δ 0.069, 0.078, 0.089, and 0.133 (s, total 6H, diastereotopic CH$_3$ of silyl ether), 0.870 and 0.875 (s, total 9H) 1.65-1.83 (m, 2H); 2.54 (m, 4H), 3.25 and 3.35 (d, total 1H), diastereomeric OH), 3.19-4.46 (series of m, total 2H, protons α to OH and silyl ether), 5.15 (s, 1H), 7.35 (m, 5H).

$^{13}$C (CDCl$_3$) δ −4.87, −5.03, −5.09, 17.60, 17.65, 25.49, 41.71, 41.96 41.98, 42.20, 42.91, 43.43, 51.18, 64.56, 65.22, 66.09, 66.93, 67.32, 127.92, 128.00, 128.29, 135.51, 171.32, 171.60, 171.69, 171.76

MS M/Z 353 (M-t butyl), IMS (ammonia) M/Z 428 (M=NH$_4$+).

C. Preparation of β-(t-butyldimethylsilyloxy)-δ-hydroxypimelic acid N-(benzyloxy)amide, monomethyl ester The alcohol-diester (7.27 g, 17.7 mmol) was dissolved in MeOH (50 ml) and to this added 10% Pd-C (20 mg). The reaction was placed under an atmosphere of H$_2$ (electrolytically generated), and stirred for 12 hr. The catalyst was removed by filtration through celite and the solvent removed in vacuo. The resulting crude oil was dissolved in THF (70 ml) and to this was added N-hydroxysuccinimide (2.23 g, 19.4 mmol). This solution was cooled to 0° C. and dicyclohexylcarbodiimide (4.0 g, 19.4 mmol) added. After 2 hr O-benzylhydroxylamine (2.75 g, 22.3 mmol) was added and the reaction allowed to warm to room temperature and then stirred for 15 hr. The precipitated dicyclohexylurea (DCU) was removed by filtration, and the solvent removed in vacuo. The residue was taken up in ethyl acetate (100 ml) and placed in a refrigerator (0° C.) overnight. Additional crystalline DCU was filtered off, the solvent removed in vacuo, and the crude product purified by flash chromatography (gradient 0.5:10, 0.7:10, 1:10 THF/CH$_2$Cl$_2$). The fractions were checked by HPLC (Alltech 5μ silica, 20:1 CH$_2$Cl$_2$/isopropanol, 1 ml/min) and pure fractions of the hydroxamate (rt=8 min) combined for an analytical sample. Obtained were 2.49 g of an oil shown to contain a small amount of the corresponding lactone of the hydroxamate (rt=6 min). This oil was used in the next step without any further purification. R$_f$=0.25 (1:9 THF/CH$_2$Cl$_2$); IR (thin film) 3425, 3210, 2960, 2940, 2860, 1740, 1655 cm$^{-1}$.

$^1$H NMR (CDCl$_3$ all signals were broad and integrals are approximate)0.072-0.083 (overlapping s, 6H), 0.86 (s, 9H), 1.67 (m, 2H), 2.23 (m, 2H), 2.53 (m, 2H), 3.65 (s, 3H), 3.82, 3.96 (broad s, 1H), 4.07, 4.19 (m. 1H), 4.31, 4.42 (M, 1H), 4.90 (s, 2H), 7.37 (m, 5H), 9.02 (s, 1H); MS(m/z) 425, 368 (M-tBu), 203, 91; high resolution MS calcd for C$_{21}$H$_{35}$NO$_6$Si 425.2234, found 425.2233.

D. Preparation of methyl 4-(1-benzyloxy-2-oxo-4-azetidinyl)-β-(t-butyldimethylsilyloxy)butyrate The hydroxamate (536 mg, 1.26 mmol) was dissolved in THF (5 ml) and solid Ph$_3$P (500 mg, 1.9 mmol) added. The solution was cooled to −10° C. and diethyl azodicarboxylate (DEAD) (0.300 ml, 1.9 mmol) was added dropwise. The reaction was stirred for 45 min at −10° C. and then for two hours at room temperature. The solvent was removed in vacuo and the residue filtered through a plug of silica, concentrated and the remaining Ph$_3$P=O precipitated using ethyl acetate/hexanes. After filtration and removal of solvents the oil obtained was purified by radial chromatography (4 mm plate, 4:1 then 3:1 hexanes/ethyl acetate) which after rechromatography of the mixed fractions gave a colorless oil (0.339 g, 66%). Preparative HPLC (Alltech 10μ silica 250 mm×10 mm, 5% ispropanol in hexane, 2 ml/min) provided analytical samples of the two diastereomers. Material for $^{13}$C NMR analysis was obtained by radial chromatography using gradient elutions of 8:1, 6:1 and then 4:1 hexanes:ethyl acetate (v:v), checking the fractions by HPLC analysis. Combination of fractions enriched in each diastereomer afforded material ≧85% pure by HPLC.

Major diastereomer: IR (thin film) 2960, 2940, 2860, 1775, 1740 cm$^{-1}$.

$^1$H NMR (CDCl$_3$) 1.52 (m, 1H), 1.91 (dt, 1H, J=4.0, 4.3, 14.0), 2.78 dd, 1H, J=5.1, 13.7), 3.64 (m, 1H), 3.67 (s, 3H), 4.12 (m, 1H), 4.96 (s, 1H), 4.97 (s, 1H) 7.39 (m, 5H).

$^{13}$C NMR (CDCl$_3$) −4.66, −4.86, 17.74, 25.62, 39.26, 39.89, 42.40, 51.53, 55.04, 67.04, 78.27, 128.53, 128.89, 129.30, 135.19, 164.20. 171.14.

Minor diastereomer: IR (thin film) 2960, 2940, 2860, 1780, 1740 cm$^{-1}$.

$^1$H NMR (CDCl$_3$) 1.49 (ddd, 1H, J=4.6, 9.4, 14.0), 1.89 (ddd, 1H, J=3.9, 6.7, 14.0), 2.30 (dd, 1H, J=6.2, 15.1), 2.42 (dd, 1H, J=6.3, 15.1), 2.38 (dd, 1H, J=2.4, 13.6), 2.74 (dd, 1H, J=5.0, 13.6), 3.61 (m, 1H), 3.67 (s, 3H), 4.13 (m, 1H), 4.94 (s 1H) 4.95 (s, 1H), 7.39 (m, 5H).

$^{13}$C NMR (CDCl$_3$) −4.78, −4.94, 17.23, 25.58, 38.33, 39.81, 42.14, 51.47, 54.64, 66.56, 78.09, 128.51, 128.88, 129.23, 135.23, 169.93, 171.12.

High resolution MS calcd for C$_{21}$H$_{33}$NO$_5$Si (as a mixture of diastereomers) 407.2128, found 407.2127.

E. Desilylation of D, methyl 4-(1-benzyloxy-2-oxo-4-azetidinyl)-β-hydroxybutyrate To a stirred solution of D as a mixture of diastereomers (339 mg, 0.80 mmol) in THF (2 ml) was added acetic acid (46 μl, 0.80 mmol) followed by tetrabutylammonium fluoride (2.4 ml of a 1M solution in THF, 2.4 mmol). The resulting orange solution was stirred for 18 hr., concentrated to one half volume and partitioned between ethyl acetate (15 ml) and brine (15 ml). The layers were separated and the aqueous layer extracted with ethyl acetate (2×15 ml). The organic layers were combined, dried (MgSO$_4$), and the solvents were removed under reduced pressure to give an oil which was flushed through a plug of silica eluting with ethyl acetate. Concentration and flash chromatography (3:1 hexanes/ethyl acetate) of the oily residue, provided the alcohol (202 mg., 86%), as a pale yellow oil. Analytical samples of the diastereomeric alcohols for $^1$H NMR were obtained by desilylation of the pure silyl ethers. Material for $^{13}$C NMR was obtained from mixtures which were ≧85% diastereomeric purity.

Major diastereomer: IR (CHCl$_3$) 3530, 3020, 1960, 1765, 1725 cm$^{-1}$.

$^1$H NMR (CDCl$_3$) 1.6 (m, 1H), 1.85 (m, 1H), 2.37 (overlapping pairs of dd, 2H), 2.42 (dd, 1H, J=2.3, 13.8), 2.80 (dd, 1H, J=5.2, 13.8), 3.00 (d, 1H, J=3.6), 3.72 (s, 3H), 3.0 (s, 3H), 4.06 (m, 3H), 4.97 (apparent d, 2H), 7.93 (m, 5H).

$^{13}$C NMR (CDCl$_3$/TMS) 38.42, 39.19, 41.34, 51.51, 56.15, 65.36, 77.82, 126.35, 128.72, 129.19, 134.98, 164.09, 172.33.

Minor diastereomer: IR (CHCl$_3$) 3520 (br), 3030, 2960, 1770, 1730.

$^1$H NMR (CDCl$_3$) 1.43 (ddd, 1H, J=3.4, 7.7, 14.4), 1.84 (ddd, 1H, J=4.6, 8.5 14.5), 2.37 (s, 1H), 2.39 (s, 1H), 2.43 (dd, 1H, J=2.4, 13.7), 2.29 (dd, 1H, J=5.2, 13.7), 3.06 (d, 1H, J=3.7), 3.72 (s, 3H), 3.75 (m, 1H), 3.99 (m, 1H), 4.95 (s, 1H), 4.96 (s, 1H), 7.39 (m, 5H).

$^{13}$C NMR (CDCl$_3$) 37.73, 38.49, 41.11, 51.60, 54.99, 64.95, 77.98, 128.42, 127.78, 129.14, 135.06, 164.10, 172.38.

F. Preparation of methyl 4-(1-benzyloxy-2-oxo-4-azetidinyl)-β-ketobutyrate

A solution of pyridine (0.679 ml, 8.4 mmol) in CH$_2$Cl$_2$ (10 ml) was cooled to 0° C. (external temp.) and finely powdered CrO$_3$ (423 mg, 4.23 mmol) was added against a positive flow of inert gas. The nonhomogeneous dark burgundy solution was allowed to warm to room temperature (23° C.), stirred for 15 min, cooled to 0° C. at which time the alcohol E (205 mg 0.7 mmol) in CH$_2$Cl$_2$ (1 ml) was added via cannula, along with a 0.5 ml rinse of the flask. The resulting dark solution was stirred at 0° C. for 15 min. and then at RT for 1 hr. The reaction was concentrated to approximately half the volume under reduced pressure, diluted with Et$_2$O (20 ml) and filtered through celite. The remaining precipitate was rinsed with several portions of ether and filtered through celite. Removal of the solvent under reduced pressure and removal of pyridine under high vacuum (0.5 torr, 1 hr.) gave a brown oil which was filtered through a plug of silica eluting with ethyl acetate. Concentration of this solution in vacuo gave a pale yellow oil (147 mg, 72%) of the β-ketoester F.

IR (CHCl$_3$) 3010, 2960, 1770 (broad), 1720 cm$^{-1}$.

$^1$H NMR (CDCl$_3$) 7.38 (m, 5H), 4.91 (d, 1H, J=10.9), 4.85 (d, 1H, J=10.9, 4.02 (m, 1H), 3.69 (s, 3H), 3.41 (s, 1H), 3.40 (s, 1H), 2.84 (dd, 1H, J=5.3, 13.9), 2.81 (dd, 1H, J=6.3, 18.0), 2.65 (dd, 1H, J=6.8, 18.0), 2.33 (dd, 1H, J=2.4 13.9).

$^{13}$C(CDCl$_3$/TMS) 38.11, 45.05, 49.06, 52.37, 52.49, 77.86, 128.61, 128.97, 129.41, 135.16, 164.07, 167.07, 199.86.

High resolution MS calcd for C$_{15}$H$_{17}$NO$_5$ 291.1107, found 291.1110.

G. Preparation of title compound

The β-keto ester F (45 mg, 0.15 mmole) was dissolved in one milliliter of acetonitrile and the solution cooled to a temperature between 0° C. and 5° C. To the cold solution was added 4-carboxybenzenesulfonyl azide (37.5 mg, 0.165 mmole, 1.1 eq) and diisopropylethylamine (31 μl, 0.18 mmole, 1.2 eq) was added dropwise via syringe. After 15 min a precipitate had formed and the reaction mixture was placed in the freezer (0° C.) for 14 hours. The brown reaction mixture was filtered to remove the preciptate and the filtrate was evaporated to a brown oil. The brown oil was chromatographed through a 10 cm×1.2 cm column of silica and the column eluted with 2:1, v:v, hexanes:acetone. The brown color remained at the top of the column and the yellow eluate was collected and concentrated by evaporation. The concentrate was rechromatographed over silica and the product eluted with 3:1, v:v, hexanes:acetone. The eluate was evaporated under vacuum to give 41 mg of the diazo ester as an oil (86% yield) having the following spectral properties.

IR (thin film): 2960, 2140, 1775, 1720, 1650, 1435, 1315 and 1210 cm$^{-1}$.

$^{13}$C(CDCl$_3$/TMS): 38.16, 42.87, 52.37, 53.03, 76.25, 77.99, 128.55, 128.89, 129.31, 135.12, 161.35, 163.98 and 189.02.

300 MHz NMR (CDCl$_3$): 2.42 (dd, 1H, J=2.4, 13.9), 2.87 (dd, 1H, J=5.2, 1.39), 3.00 (dd, 1H, J=6.7, 17.5), 3.29 (dd, 1H, J=6.3, 17.5) 3.84 (s, 3H), 4.13 (m, 1H), 4.91 (d, 1H, J=10.8), 4.96 (d, 1H, J=10.8) and 7.37 (m, 5H).

Preparation 2

Methyl 5-(1-benzyloxy-2-oxo-4-azetidinyl)-α-diazo-β-ketovalerate

A. Succinic acid mono-(2-trimethylsilyl)ethyl ester

Succinic anhydride (6.0 g, 60 mmole) was dissolved in dry tetrahydrofuran (25 ml) and to this solution was added 2-trimethyl-silylethanol (9.03 ml, 63 mmole) followed by triethylamine (9.2 ml, 66 mmole) and 4-dimethylaminopyridine (366 mg, 2.9 mmole). The reaction was stirred for 20 hours at room temperature. The THF was then removed by rotary evaporation and the residue dissolved in 300 ml of ether. This was washed with 1N HCl (2×100 ml), brine (100 ml) and then dried over MgSO$_4$. The drying agent was filtered off and the filtrate concentrated (rotary evaporation, high vacuum 0.1 torr., 12 h) to give 12.94 g (98%) of the half ester as a colorless oil. This product was of high purity and used directly without any further purification.

IR (thin film): 3500–2700 (broad), 1745, and 1720 cm$^{-1}$.

$^{13}$C (CDCl$_3$ref.=77.00): −1.74, 17.05, 28–87, 28.75, 62.88, 172.24, 177.50.

1H NMR (CDCl$_3$): 0.036 (s, 94H), 0.99 (m, 2H), 2.62 (m, 4H), 4.20 (m, 2H).

B. β-Ketoadipic acid benzyl, 2-(trimethylsilyl)ethyl diester

The acid-ester A (4.46 g, 20.4 mmole) was dissolved in 50 ml of tetrahydrofuran and carbonyldimidazole (3.48 g, 21.4 mmole, 1.05 eq.) was added and the reaction mixture stirred for 1.5 hours to provide the imidazole active ester. In a separate flask the monobenzyl ester of malonic acid (4.36 g, 22.4 mmole, 1 eq.) was dissolved in 60 ml of tetrahydrofuran and the solution cooled to −78° C. Di-n-butylmagnesium (22.44 ml, 11.22 mmole, 0.55 eq.) was added and the mixture was stirred for 15 min at −78° C. and at room temperature for 1.5 hours. The reaction mixture of the magnesium salt of the monobenzylmalonate was evaporated and the solution of the imidazole active ester was added to the salt via cannula. After about 12 hours when a thin layer chromatogram (tlc) indicated some unreacted imidazole active ester, the reaction mixture was heated to about 40° C. for 8 hours. Chromatography (tlc) indicated only a very small amount of imidazole ester remaining. The reaction mixture was evaporated in vacuo and the residue dissolved in 200 ml of diethyl ether. The solution was washed twice with 100 ml of citric acid solution, once with 100 ml of saturated sodium bicarbonate, once with 100 ml of brine, was dried over $MgSO_4$, filtered and evaporated to yield 6.51 g of the product, β-ketoadipic acid benzyl, 2-(trimethylsilyl) ethyl diester, as a light yellow oil.

$^1H$ NMR ($CDCl_3$): 0.34 (s, 9H), 0.97 (m, 2H), 2.57 (apparent t, 2H, J=6.5, 6.7), 2.83 (apparent t, 2H, J=6.4, 6.2), 3.54 (s, 2H), 4.15 (M, 2H), 5.17 (s, 2H), 7.35 (s, 5H).

$^{13}C$ ($CDCl_3$/ref=77.00) −1.81, 16.94, 17.74, 37.05, 48.82, 62.54, 66.69, 127.99, 128.06, 128.26, 135.09 166.48. 172.05, 200.57.

IR (thin film): 2960k 1725 (broad), 1200, 1120 $cm^{-1}$.

C. β-Hydroxyadipic acid benzyl, 2-(trimethylsilyl)ethyl diester

The β-keto ester B (15 g, 42.8 mmol) was dissolved in dry ethanol (50 ml) and cooled to −30° C. (bath temperature). To this solution was added powdered sodium borohydride (486 mg, 12.84 mmol). This solution was stirred for 30 min at −30° C. and then allowed to warm to −20° C. over a 15 min period. Thin layer chromatography indicated consumption of starting material. The reaction was quenched at −20° C. with 300 ml of saturated sodium chloride solution which had been pre-cooled to 0° C. The resulting mixture was then extracted while cold with ether (3×250 ml). The ether layers were combined and washed with water (2×100 ml), brine (100 ml) and then dried over $MgSO_4$. The drying agent was removed by filtration and the solvent removed by rotary evaporation to give the crude β-hydroxy diester as a light yellow oil. The crude product was used directly in the next step without any further purification. An analytical sample was prepared by flash chromatography on silica gel (3:1 hexanes:ethyl acetate; v:v).

$^1H$ ($CDCl_3$) 0.038 (s, 9H), 0.98 (m, 2H), 1.79 (m, 2H), 2.80–2.52 (M, 4H), 3.55 (d, 1H), 4.05 (m, 1H), 4.17 (M, 2H), 5.15 (s, 2H), 7.35 (s, 5H).

$^{13}C$ ($CDCl_3$/ref=77.00) −1.67, 17.12, 30.38, 31.23, 41.36. 62.47, 66.28, 67.04, 128.03, 128.13, 128.39, 135.45. 173.57, 172.09.

IR (thin film) 3460 (broad), 2960, 1730, 1250, 1170 $cm^{-1}$.

D. 2-(Trimethylsilyl)ethyl 3-(1-benzyloxy-2-oxo-4-acetidinyl) proprionate

The β-hydroxy diester C (193 mg, 0.55 mmole) was dissolved in 4 ml of ethyl acetate and a few milligrams of 10% Pd/C catalyst were added. The reduction mixture was placed under hydrogen under balloon pressure and stirred for about one hour. When tlc showed the presence of a quantity of starting material the reduction mixture was sonicated for 1.5 min to clean the catalyst and hydrogenation was continued for one hour. The reduction mixture was filtered through a filter aid and the filtrate concentrated under vacuum. The debenzylated half acid ester was dissolved in 3 ml of THF and the solution cooled to 0° C. To the cold solution was added N-hydroxysuccinimide (69 mg, 0.60 mmole, 1.1 eq.) followed by dicyclohexylcarbodiimide (124 mg, 0.60 mmole, 1.1 eq) and the solution was stirred for about 30 min. Next, benzyloxyamine (74 mg, 0.6 mmole, 1.1 eq) was added and the reaction mixture was stirred for 30 min at 0° C. and with warming for 16 hours at room temperature. The dicyclohexylurea side product was filtered, the filtrate concentrated by evaporation and the residue chromatographed on silica (3:1, hexanes:acetone, v:v) to yield an oil. A small portion of the oil was crystallized from ethyl acetate-hexanes as a white powder or preferably from methylene chloride-hexanes which provided small white plates melting at about 66° C. to about 68° C. The remaining product (oil) solidified under high vacuum yielding 143 mg (71% yield) of 2-(trimethylsilyl)ethyl β-hydroxyadipic acid N-benzyoxamide.

$^1H$ NMR ($CDCl_3$)-(all signals were very broad, integrals were approximate) 0.040 (s, 9H), 0.98 (m, 2H), 1.75 (m, 2H), 2.43–2.46 (m, 3H), 3.72 (m, 1H), 3.99 (m, 1H), 4.17 (m, 1H), 4.90 (s, 2H), 7.38 (m, 5H), 8.73 (s, 1H).

$^{13}C$ ($CDCl_3$/ref.=77.00, $CDCl_3$triplet) −1.67, 17.09, 30.45, 31.51, 40.02, 62.62, 67.48, 77.97, 128,32, 128.46, 128.99, 135.11, 169.55, 173.92.

IR (KBr): 3420, 3200, 2960, 1725, 1645, 1630 $cm^{-1}$.

The adipic N-benzyloxyamide half 2-(trimethylsilyl)ethyl ester prepared as described above (97 mg, 0.26 mmole) was dissolved in 2.5 ml of THF and triphenylphosphine (81 mg, 0.31 mmole, 1.2 eq.) was added. The solution was cooled to −20° C. and diethyl azodicarboxylate (49 μl, 0.31 mmole, 1.2 eq.) was added to the cold solution which was stirred at −20° C. for 30 min and then at room temperature for about 15 hours. Tlc indicated that all of the hydroxamate was consumed. The reaction mixture was evaporated and the residue containing the β-lactam product was chromatographed over silica (2:1, hexanes:ethyl acetate, v:v) providing 80 mg (88% yield) of the product as a faint yellow oil.

$^1H$ NMR ($CDCl_3$): 0.046 (s, 9H), 0.97 (m, 2H), 1.71–1.82 (m, 1H), 1.89–2.00 (m, 1H), 2.28 (m, 2H) overlapping with 2.31 (dd, 1H, J=2.3, 13.7), 2.73 (dd, 1H, J=5.2, 13.7), 3.56 (m, 1H), 4.15 (m, 2H), 4.96 (dd, 2H), 7.40 (m, 5H).

$^{13}C$ ($CDCl_3$/ref.=77.00, center of $CDCl_3$ triplet) −1.67, 17.13, 27.48, 30.17, 37.43, 56.71, 62.67, 77.94, 128.43, 128.79, 129.11, 135.01, 163.67, 172.27.

IR (thin film): 2960, 1775, 1730, 1250, 1170 $cm^{-1}$.

E. Methyl 5-(1-benzyloxy-2-oxo-4-azetidinyl)-β-ketovalerate

The N-benzyloxyazetidinone 2-(trimethylsilyl)ethyl ester D (94 mg, 0.27 mmole) was treated with tetrabutylammonium fluoride (0.81 ml, 0.81 mmole, 3 eq.) in one ml of DMF. Gas evolution began immediately and after about 5 min tlc showed that no starting ester remained. The mixture was poured into 20 ml of 10% citric acid solution and the solution extracted four times with 15 ml portions of methylene chloride. The extracts were combined, dried over $MgSO_4$, filtered and evaporated to provide 85 mg of the crude deesterification product, 3-(1-benzyloxy-2-oxo-4-azetidinyl)propionic acid, as an oil. The oil was filtered through a plug of silica and eluted with ethyl acetate. The solvent was evaporated to provide 42 mg (63% yield of the product β-lactam acid as a pale yellow oil. A small amount of this oil solidified upon standing at room temperature, serving as seed crystals for crystallization of the remaining oil from ether:hexanes to give colorless plates, mp 62°–64° C.

$^1H$ NMR ($CDCl_3$): 1.72–1.84 (m, 1H), 1.87–1.99 (m, 1H), 2.32 (dd, 1H, J=2.4, 13.8), 2.36 (m, 2H), 2.75 (dd,

1H, J=5.2, 13.8), 3.55 (m, 1H), 4.96 (dd, 2H), 7.39 (m, 5H).

$^{13}$C (CDCl$_3$/TMS Ref.) 27.37, 29.94, 37.55, 57.01, 78.27, 128.69, 129.12, 129.37, 135.03, 164.13, 177.53.

IR (thin film): ca 3700–2500 (broad), 2940, 1750 (broad) cm$^{-1}$; IR (CCl$_4$): 1775. 1710 cm$^{-1}$.

The β-lactam acid prepared as described above (253 mg, 1.02 mmole) was dissolved in THF and the solution cooled to 0° C. Carbonyldiimidazole (CDI) (187 mg, 1.16 mmole, 1.1 eq.) was added and the solution was stirred for 15 min at 0° C. and at room temperature for 2 hours to form the imidazole active ester. To the solution was added 145 mg of the magnesium salt of monomethylmalonate. The reaction mixture was stirred for 15 hours and evaporated. The residue containing the product was treated with 30 ml of diethyl ether and 20 ml of 10% citric acid solution in water. The organic layer was separated, washed with 20 ml of 10% citric acid solution, 20 ml of a saturated solution of sodium bicarbonate, dried over MgSO$_4$, and evaporated to yield a yellow-residue. The residue was purified by chromatography over silica (1:1.5, hexanes:ethyl acetate, v:v) to give 235 mg (76% yield) of the β-keto ester product, methyl 5-(1-benzyloxy-2-oxo-4-azetidinyl)-β-ketovalerate, as a pale yellow oil.

$^1$H NMR (CDCl$_3$): 1.72–1.95 (m, 2H), 2.29 (dd, 1H, J=2.4, 13.8), 2.53 (m, 2H), 2.73 (dd, 1H, J=5.2, 13.8), 3.41 (s, 1H), 3.65 (m, 1H) 3.73 (s, 3H), 4.95 (dd, 2H), 7.40 (m, 5H).

$^{13}$C (CDCl$_3$/TMS ref.) 25.83, 37.47, 48.69, 52.22, 56.59, 77.96, 128.59, 128.95, 129.25, 135.24, 163.92, 167.43, 201.40.

IR (thin film) 3040, 2960, 1770, 1750 (shoulder), 1715, 1430, 1320, 1040 cm$^{-1}$.

F. α-Diazo-β-keto-β-lactam (title compound)

The β-ketoester E (35 mg, 0.11 mmole) was dissolved in one milliliter of acetonitrile and the solution cooled to 0° C. in an ice-salt bath. To the cold solution was added p-carboxybenzenesulfonyl azide (27 mg, 0.12 mmole, 1.1 eq.) followed by diisopropylc ethylamine (25 µl, 0.14 mmole, 1.3 eq.). The reaction mixture was stirred for one hour at 0° C. and for 12 hours at room temperature. The white precipitate which had formed was filtered and the filtrate was evaporated. The residue was chromatographed on silica (1:1, hexanes:ethyl acetate, v:v) to give 35 mg (92% yield) of the title compound, methyl 5-(1-benzyloxy-2-oxo-4-azetidinyl)-α-diazo-β-ketovalerate, as a very pale, clear, yellow oil.

$^1$H NMR (CDCl$_3$) 1.82 (m, 1H), 1.96 (m, 1H), 2.35 (dd, 1H, J=2.4, 13.7), 2.73 (dd, 1H, J=5.2, 13.70, 2.85 (t, 2H, J=7.5), 3.58 (m, 1H), 3.84 (s, 3H), 4.96 (dd, 2H), 7.38 (m, 5H).

$^{13}$C (CDCl$_3$/TMS ref) 26.94, 36.17, 37.79, 52.27, 57.11, 75.80, 78.21, 128.59, 128.92, 129.33, 135.23, 101.55, 164.00, 191.06.

IR (thin film) 3040, 2960, 2140, 1775, 1720, 1655 cm$^{-1}$.

EXAMPLE 1

Methyl 1-carba(dethia)penam-2-oxo-3-carboxylate via 1-benzyloxyazetidinone-2

Methyl 4-(1-benzyloxy-2-oxo-4-azetidinyl)-α-dizao-β-ketobutyrate, prepared as described above in Preparation 1 (60 mg, 0.19 mmol) was dissolved in dry benzene (4 ml) and the benzene rotary evaporated to remove any trace amounts of water. The oil was dissolved in dry methylene chloride (4 ml 0.047M) and to this solution was added Rh$_2$(OAc)$_4$ (0.80 mg, 1 mol %), which was then refluxed for 1.25 hr. The solvent was removed by rotary evaporation followed by high vacuum (0.5 torr., 1 h.) to remove benzaldehyde. The resulting brown oil was flash chromatographed on silica gel (15×1 cm column, 2:1 benzene:ethyl acetate; v:v) to give 13 mg (37%) of the penam as a faint yellow oil.

300 MHz $^1$H NMR (CDCl$_3$): 2.41 (dd, 1H, J=18.8, 7.8), 2.92 (ddd, 1H, J=18.8, 6.8, 6.7), 2.97 (dd, 1H, J=16.1, 2.1), 3.66 (dd, 1H, J=16.2, 5.0), 4.18 (m, 1H), 3.80 (s, 3H), 4.71 (s, 1H).

IR (CCl$_4$): 1785, 1775, 1750.

Mass Spectrum: (CI with isobutane): m/e 184 (M+1).

$^{13}$C NMR (CDCl$_3$) 41.80, 46.61, 48.44, 53.17, 64.35, 165.58, 172.36, 207.08.

HRMS: calcd. for C$_8$H$_9$NO$_4$ 183.0532, found 183.0534.

EXAMPLE 2

Methyl 3-Hydroxy-1-carba-(dethia)-3-cephem-4-carboxylate

Methyl 5-(1-benzyloxy-2-oxo-4-azetidinyl)-60-diazo-β-ketovalerate, prepared as described above in Preparation 2, is dissolved in methylene chloride and treated with Rh$_2$(OAc)$_4$ to provide the title compound and benzaldehyde, the expected side product.

EXAMPLE 3

Methyl 1-Carba(dethia)penam-2-oxo-3-carboxylate via 1-methoxyazetidinone-2

The silyl protected N-benzyloxy-β-lactam prepared as described above in Preparation 1 D (600 mg, 1.47 mmol) was dissolved in 5 ml of ethyl acetate and 50 mg of 10% Pd-on-carbon catalyst were added to the solution. The mixture was placed under an atmosphere of hydrogen using a balloon. After 6 hours the hydrogenolysis of the benzyl group was incomplete and 50 mg of additional catalyst suspended in 1 ml of ethyl acetate was added. The reaction was complete after 4 additional hours. The catalyst was removed by filtration (celite) and the solvent removed by rotary evaporation to provide a pale yellow oil. The oil was dissolved in 8 ml of acetonitrile, the solution cooled to 0° C. and cesuim carbonate (718 mg, 2.2 mmol) was added followed by methyl iodide (0.200 ml, 3.2 mmol) which was filtered through activated alumina before use. After stirring for 2.5 h at 0° C. the reaction mixture was diluted with 60 ml of diethyl ether and the diluted mixture washed with 10% citric acid, 5% sodium bicarbonate and with brine and was dried over magnesium sulfate. After filtration and evaporation of solvent 474 mg of the crude O-methylated product, methyl 4-(1-methoxy-2-oxo-4-azetidinyl)-β-t-butyldimethylsilyloxy)butyrate, were obtained as an oil. The oil was dissolved in 1 ml of tetrahydrofuran (THF) and the solution cooled to 0° C. Acetic acid (81 µl, 1.42 mmol) was added followed by tetrabutylammonium fluoride (3.55 ml of a 1M solution in THF, 3.55 mmol). The resulting orange solution was allowed to stir for 1 h at 0° C. and then at room temperature (about 23° C.) for 14 h. The solution was evaporated to remove THF and the brown residue partitioned between ethyl acetate (20 ml) and water 20 ml). The aqueous layer was separated and extracted with 20 ml of additional ethyl acetate. The combined ethyl acetate extracts were washed with 20 ml of brine, dried (MgSO$_4$) and evaporated to provide 100 mg of the desilylated product, methyl 4-(1-methoxy-2-oxo-4-azetidinyl)-5-hydroxybutyrate. The above extraction process of the aqueous layers was repeated to yield an additional 80 mg of the desilylated product. The aqueous layers were then extracted with several portions of methylene chloride and all extracts combined and evaporated to yield 279 mg of a light brown oil. Flash chromatography on silica (2:1 hexanes:acetone) gave 246 mg (78% for three steps) of the desilylated product as a pale yellow oil.

IR (thin film) 3440 (br), 2960, 1770, 1740 (shoulder) cm$^{-1}$.

$^1$H NMR (CDCl$_3$) δ 1.64–2.18 (series of m, total 2H, protons α to OH and lactam ring), 2.53 (m, 3H), 2.90 and 2.93 (dd, total 1H, J=5, 14, diastereomeric cis C-3 ring protons), 3.32 and 3.33 (broad s, 1H, diastereomeric hydroxyl protons), 3.73 (s, 3H), 3.81 and 3.82 (s, total 3H), 4.14 and 4.24 (m, total 1H, C-4 protons).

$^{13}$C NMR (CDCl$_3$) δ 37.61, 38.31, 38.78, 39.50, 41.28, 41.45, 51.52, 53.89, 52.94, 63.40, 63.53, 64.97, 65.43, 163.48. 163.59, 172.22, 172,30.

HRMS calcd. for C$_9$H$_{15}$NO$_5$: 217.0950, found 217.0951.

The desilylated 1-methoxyazetidinone was stirred with 2 g of activated 3 A molecular sieves in 1 ml of dry CH$_2$Cl$_2$ for 12 h prior to use in order to remove trace amounts of water. To a solution of pyridine (1.11 ml, 13.68 mmol) in CH$_2$Cl$_2$ (15 ml) at 0° C. was added powdered CrO$_3$ (683 mg, 6.84 mmol). The resulting burgundy solution was then allowed to warm to room temperature, stirred for 15 min, and then cooled to 0° C. The alcohol was added via cannula and stirred for 30 min and then warmed to room temperature. After several hours (TLC monitor) the reaction was diluted with ether (60 ml) and filtered through celite. Concentration of this filtrate gave a brown oil which was placed under high vacuum to remove pyridine. The residue was then placed on a silica gel column (15×2 cm) and the column quickly eluted with ethyl acetate (100%) taking ~20 ml fractions. Removal of solvent from the fractions containing product gave 149 mg of the β-ketoester, methyl 4-(1-methoxy-2-oxo-4-azetidinyl)-β-ketobutyrate, (61%) as a pale yellow oil. No further purification was attempted. This material is of sufficient purity to use in the next step.

IR (thin film) 2960, 1775, 1715 cm$^{-1}$.

$^1$H NMR (CDCl$_3$) δ 2.41 (dd, 1H, J=2.4, 14), 2.91 (dd, 1H, J=6.4, 18), 2.94 (dd, 1H. J=5.2, 14), 3.13 (dd, 1H, J=6.6, 18), 3.53 (d, 2H), 3.75 (s, 3H), 3.76 (s, 3H), 4.31 (m, 1H).

$^{13}$C (CDCl$_3$) δ 37.78, 45.006, 48.85, 51.24, 52.18, 63.27, 163.19, 166.92, 199.67.

HRMS calcd. 215.0794, found 215.0792.

The β-ketoester (149 mg, 0.69 mmol) was dissolved in CH$_3$CN (2 ml) and cooled to −10° C. and to this added p-carboxybenzenesulfonyl azide (174 mg, 0.77 mmol) followed by the dropwise addition of diisopropylethylamine (145 μl, 0.84 mmol) over a 10 min period. The reaction was stirred for 2 h, not allowing the temperature to exceed −5° C. The reaction was then allowed to stand in a freezer at −10° C. for 12 h. The precipitate was removed by filtration (celite) and the filtrate concentrated to give a dark brown oil. The crude oil was eluted through a short column of silica (1:1 hexanes-/acetone) to give a yellow oil after concentration. Flash chromatography on silica gel (2:1 hexanes-acetone) gave 139 mg (83%) of the diazo compound methyl 4-(1-methoxy-2-oxo-4-azetidinyl)-β-keto-α-diazobutyrate as a light yellow oil which solidified upon standing at 0° C. overnight. An analytical sample was obtained by recrystallization from ether-hexanes: mp 55°–57° C.

IR (KBr) 2980, 2950, 2150, 2150, 1790, 1770, 1715, 1650 cm$^{-1}$.

$^1$H NMR (CDCl$_3$) δ 2.47 (dd, 1H, J=2.4, 13.9), 2.93 (dd, 1H, J=5.2, 13.9), 3.13 (dd, 1H, J=6.6, 17.5), 3.49 (dd, 1H, J=6.4, 17.5), 3.79 (s, 3H), 3.86 (s, 3H), 4.35 (m, 1H).

$^{13}$C (CDCl$_3$) δ 37.91, 42.86, 51.88, 52.19, 63.49, 75.99, 161,24, 163.24, 188.79.

HRMS calcd. 241.0899, found 241.0700.

The α-diazo-β-keto ester was dissolved in dry methylene chloride and a catalytic amount of rhodium tetraacetate was added. The mixture was heated at the reflux temperature to provide the title penam ester and formaldehyde.

EXAMPLE 4

Methyl 1-Carba(dethia)-2-oxopenam-3-carboxylate via 1-methoxymethoxyazetidinone-2

The silyl protected N-benzyloxy-β-lactam D, Preparation 1 (986 mg, 2.37 mmol) was dissolved in ethyl acetate (10 ml) and to this solution added 10% Pd-C (100 mg). After placing under an atmosphere of H$_2$ using a balloon, the reaction was stirred for 2.5 hours at which time the catalyst was removed by filtration through celite and the solvent removed by rotary evaporation. The oil obtained was dissolved in CH$_3$CN (4 ml) and cooled to 0° C. CsCO$_3$ (1.16 g, 3.55 mmol) was added followed by the dropwise addition of chloromethylmethyl ether (260 μl, 3.31 mmol). The reaction was complete after 45 min. The reaction was concentrated to near dryness and then partitioned between ether (50 ml) and water (30 ml). The layers were separated and the aqueous layer extracted with ether (25 ml). The combined organic layers were washed with brine, dried (MgSO$_4$), and the solvent evaporated to give a light yellow oil. The crude methoxymethyl alkylated product was dissolved in THF (3 ml), cooled to 0° C., and treated with acetic acid (135 μl, 2.35 mmol) followed by tetrabutylammonium fluoride (4.74 ml of a 1M solution in THF, 4.74 mmol). After stirring 30 min at 0° C. and 8 h at room temperature the reaction was then concentrated and the crude residue was eluted through a short column of silica with ethyl acetate. The solvent was removed and the oil obtained was purified by flash chromatography on silica gel (3:1 ethyl acetate-hexanes) giving most fractions containing product contaminated with a more polar material. Rechromatography of the mixed fractions (2:1 ethyl acetate-hexanes) gave 500 mg (85% for three steps) of methyl 4-(1-methoxymethoxy-2-oxo-4-azetidinyl)-β-hydroxybutyrate as an oil.

IR (thin film) 3460 (br), 2960, 1775, 1735 cm$^{-1}$.

$^1$H NMR (CDCl$_3$) δ 1.58–2.12 (series of m, total 2H, protons α to the OH and lactam ring), 2.35 (m, 3H), 2.90 and 2.93 (dd, total 1H, J=5, 14, diastereomeric cis C-3 ring protons), 3.28 and 3.29 (apparent t, total 1H, diastereomeric hydroxyl protons), 3.53 and 3.55 (s, total 3H), 3.73 (s, 3H), 4.12 and 4.25 (m, total 1H, C-4 protons), 4.85 and 4.87 (dd, and s respectively, total 2H, methylene of ether).

$^{13}$C (CDCl$_3$) δ 37.86, 38.63, 38.72, 39.45, 41.30, 41.39, 51.69, 55.42, 55.58, 56.49, 56.65, 64.95, 65.48, 100.06. 100.21, 164.91, 172.55, 172.58

HRMS calcd. for $C_{10}H_{17}NO_6$ 247.1056, found 247.1057.

The alcohol (498 mg, 2.01 mmol) was oxidized with $CrO_3$/pyridine complex as described for the O-methyl analog to give 371 mg (75%) of the ketoester as a pale yellow oil.

IR (thin film) 2960, 1775, 1750 (shoulder), 1720 cm$^{-1}$.

$^1$H NMR (CDCl$_3$) 2.45 (dd, 1H, J=2.6, 14.1), 2.90 (dd, 1H, J=6.9, 18.1), 3.01 (dd, 1H J=5.5, 14.1), 3.20 (dd, 1H, J5.8, 18.1), 3.51 (s, 3H) overlaps with 3.51 (d, 2H), 3.76 (s, 3H), 4.29 (m, 1H), 4.76 (d, 1H, J=7), 4.86 (d, 1H, J=7).

$^{13}$C (CDCl$_3$) δ 38.09, 45.25, 48.90, 52.14, 52.70, 56.46, 99.95, 164.95, 164.46, 166.92, 199.66

The ketoester (339 mg, 1.38 mmol) was diazotized as described for the O-methyl analog. Purification by flash chromatography on silica (2:1 (hexanes-acetone) gave 3.18 mg (85%) of the diazo compound, methyl 4-(1-methoxymethyoxy-2-oxo-4-azetidinyl)-α-diazo-β-ketobutyrate, as a yellow oil.

IR (thin film) 2960, 2115, 1775, 1715, 1650 cm$^{-1}$.

$^1$H NMR (CDCl$_3$) 67 2.51 (dd, 1H), J=2.5, 14), 2.99 (dd, 1H, J=5.4, 14), 3.10 (dd, 1H, J=7.4, 17.7), 3.54 (s, 3H), 3.57 (dd, 1H, J=5.7) 3.86 (s, 3H), 4.32 (m, 1H), 4.80 (d, 1H, J=7), 4.89 (d, 1H, J=7).

$^{13}$C (CDCl$_3$) δ 38.06, 42.76, 52.07, 53.11, 56.41, 75.85, 99.79, 161,08, 164.31, 188.82.

The title compound was obtained by heating a solution of the α-diazo-β-keto ester in dry methylene chloride in the presence of a catalytic amount of rhodium tetraacetate at the reflux temperature. Methyl formate, the expected side product, was detected by NMR and confirmed by spiking with methyl formate.

We claim:

1. The process for preparing a β-lactam compound of the formula

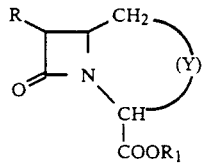

which comprises mixing in an inert solvent at a temperature between about 15° C. and about 85° C. a diazo ester of the formula

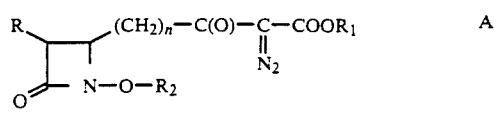

with a catalytic amount of a rhodium $C_2$-$C_{10}$ carboxylate where, in the above formulae, R is hydrogen, amino, protected amino, ethyl or hydroxyethyl; $R_1$ is a carboxy protecting group; $R_2$ is $C_1$-$C_6$ alkyl or $C_1$-$C_6$ substituted alkyl substituted by a member of the group of phenyl, carboxy, protected carboxy, hydroxy, fluoro, chloro, bromo, cyano or $C_1$-$C_3$ alkoxy; n is 1 or 2; and Y is a divalent group of the formula

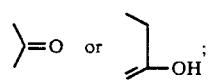

provided that, when n is 2, R is amino or protected amino.

2. The process of claim 1 wherein the catalytic amount of rhodium $C_2$-$C_{10}$ carboxylate is between about one mole percent and about ten mole percent with respect to the diazo ester.

3. The process of claim 1 wherein the catalyst is rhodium tetraacetate of rhodium octanoate.

4. The process of claim 2 wherein the catalyst is rhodium tetraacetate.

5. The process of claim 1 where, in the diazo ester n is 1.

6. The process of claim 2 where, in the diazo ester, n is 2.

7. The process of claim 3 wherein R is amino or protected amino.

8. The process of claim 3 wherein R is ethyl or hydroxyethyl.

9. The process of claim 4 wherein R is amino or protected amino.

10. The process of claim 7 wherein R is phenylacetylamino or phenoxyacetylamino.

11. The process of claim 1 wherein $R_2$ is $C_1$-$C_6$ alkyl.

12. The process of claim 9 wherein $R_2$ is methoxy.

13. The process of claim 1 wherein $R_2$ is substituted $C_1$-$C_6$ alkyl.

14. The process of claim 13 wherein $R_2$ is benzyl.

* * * * *